United States Patent
Jun

(10) Patent No.: US 10,416,104 B2
(45) Date of Patent: Sep. 17, 2019

(54) GAS SENSING DEVICE

(71) Applicant: LG INNOTEK CO., LTD., Seoul (KR)

(72) Inventor: Sung Gon Jun, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 189 days.

(21) Appl. No.: 15/323,051

(22) PCT Filed: Jul. 7, 2015

(86) PCT No.: PCT/KR2015/007001
§ 371 (c)(1),
(2) Date: Dec. 29, 2016

(87) PCT Pub. No.: WO2016/006911
PCT Pub. Date: Jan. 14, 2016

(65) Prior Publication Data
US 2017/0138878 A1    May 18, 2017

(30) Foreign Application Priority Data
Jul. 11, 2014    (KR) ......................... 10-2014-0087352

(51) Int. Cl.
G01N 33/00    (2006.01)
G01N 27/04    (2006.01)
(Continued)

(52) U.S. Cl.
CPC ......... G01N 27/04 (2013.01); G01N 33/0006 (2013.01); G08B 21/12 (2013.01); G08B 29/185 (2013.01); G08B 29/24 (2013.01)

(58) Field of Classification Search
CPC .. G01N 27/04; G01N 27/048; G01N 33/0006; G01N 33/0008; G01N 33/0062;
(Continued)

(56) References Cited

U.S. PATENT DOCUMENTS 7,554,135 B2    6/2009 Lehmann et al.
9,410,912 B2    8/2016 Yamada et al.
(Continued)

FOREIGN PATENT DOCUMENTS

CN    1616950    5/2005
CN    1685223    10/2005
(Continued)

OTHER PUBLICATIONS

Kim Soo Jong et al.: "An Environment Information Sharing System Using SmartPhone"; Proceedings of Symposium of the Korean Institute of Communications and Information Sciences; Feb. 2012; pp. 232-233; retrieved from the Internet: URL: http://www.dbpia.co.kr/Article/NODE02039157 [retrieved on Nov. 1, 2015] *p. 232* (English Abstract and Full Korean Text).
(Continued)

*Primary Examiner* — Robert R Raevis
(74) *Attorney, Agent, or Firm* — KED & Associates LLP

(57) ABSTRACT

The present invention relates to a gas sensing device comprising: a gas sensing part for outputting a gas detection result; and a correction control part for changing the value outputted from the gas sensing part to a reference value when the output value is lower than the reference value.

14 Claims, 5 Drawing Sheets

(51) Int. Cl.
*G08B 21/12* (2006.01)
*G08B 29/18* (2006.01)
*G08B 29/24* (2006.01)

(58) Field of Classification Search
CPC .............. G01N 33/0063; G01N 33/007; G01N 33/0073; G01N 27/121; G01N 33/0036–0059; G08B 21/12
USPC ............................ 73/1.06, 1.02, 23.2–31.06, 73/335.01–335.14; 338/34, 35; 324/693, 324/694
See application file for complete search history.

(56) References Cited

U.S. PATENT DOCUMENTS

| 2006/0263254 | A1 | 11/2006 | Lee | |
|---|---|---|---|---|
| 2011/0199094 | A1 | 8/2011 | Lou | |
| 2014/0079590 | A1* | 3/2014 | Rossi | A61M 1/3666 422/45 |
| 2014/0216136 | A1* | 8/2014 | Yim | G01N 33/4972 73/31.05 |

FOREIGN PATENT DOCUMENTS

| CN | 1788196 | 6/2006 |
|---|---|---|
| CN | 203083613 | 7/2013 |
| CN | 103518130 | 1/2014 |
| JP | H 11-248661 | 9/1999 |
| JP | 2002-221319 | 8/2002 |
| KR | 10-2001-0000116 | 1/2001 |
| KR | 10-2006-0035909 | 4/2006 |
| KR | 10-2010-0118729 | 11/2010 |
| KR | 10-2011-0011184 | 2/2011 |
| KR | 10-2014-0024541 | 3/2014 |

OTHER PUBLICATIONS

Yoon Choe et al.: "Ambient Urban Media Composition for Sustainable Lifestyle of Smart Green City—Based on the User Interaction with Visualization of Indoor Air Pollution"; Journal of the Architectural Institute of Korea Planning and Design; Aug. 2013; vol. 29, No. 8; pp. 123-130; retrieved from the Internet: URL: http://www.dbpia.co.kr/Article/NODE02227899 [retrieved on Nov. 1, 2015] *pp. 127, 128 and figure 7* (English Abstract and Full Korean Text).
International Search Report (with English translation) and Written Opinion dated Nov. 10, 2015 issued in Application No. PCT/KR2015/007001.
Chinese Office Action dated Sep. 26, 2018 issued in Application No. 201580037870.9.
Chinese Office Action dated May 10, 2019 issued in Application 201580037870.9.
Chinese article pp. 128-134 (full Chinese text and English Abstract).

* cited by examiner

GAS SENSING DEVICE

CROSS-REFEREMCE TO RELATED PATENT APPLICATIONS

This application is a U.S. National Stage Application under 35 U.S.C. § 371 of PCT Application No. PCT/KR 2015/007001, filed Jul. 7, 2015, which claims priority to Korean Patent Application No. 10-2014-0087352, filed Jul. 11, 2014, whose entire disclosures are hereby incorporated by reference.

TECHNICAL FIELD

A gas sensing device is disclosed herein.

BACKGROUND ART

Sensors used in detecting of gas, compounds and biomolecules have been in the limelight and many studies have been published. Among them, a gas sensor have been used in a wide range of fields such as chemistry, pharmaceuticals, environment and medical care, and it is predicted that more research will be done in the future.

A technology detecting harmful substances and pollutants in the air in real time is indispensable to maintain good living environment and working environment. Therefore, the gas sensor is installed in various places and performs an important role monitoring the harmful substances and pollutants in the atmosphere and environment in which we live.

A gas sensor device notifies the detection or concentration of gas in an installed environment to a user.

In order to provide such a function, a conventional gas sensor device is configured to output a change of resistance value so as to discriminate whether the gas is detected or not, or convert the resistance value into a voltage value through a resistance and output it.

However, the gas sensor device according to the related art sensitively responses to an external environment such as temperature and humidity, so that the user may not correctly recognize whether the gas is detected or not, and there was a problem that the user may not easily recognize whether the gas is detected or not.

DISCLOSURE

Technical Problem

The present disclosure is made to solve the above problems, and directed to correcting an output value of a gas sensor which is sensitive to an external environment such as temperature and humidity, so that a user may accurately determine whether a gas is detected or not and thus may not be mistaken.

Also, the present disclosure is directed to allowing the user to more easily detect a quality of air or a degree of gas contamination.

Technical Solution

In order to solve the above problems, a gas sensing device according to a present embodiment includes a gas sensing part outputting a result of gas sensing; and a correction control part changing an output value to a reference value when the value output from the gas sensing part is lower than the reference value.

According to another embodiment of the present disclosure, the correction control part may change the output value to the reference value when the value output from the gas sensing part is lower than the reference value.

According to another embodiment of the present disclosure, the correction control part may constantly correct the value output from the gas sensing part to the reference value.

According to another embodiment of the present disclosure, a display displaying gas detection information may be further included, and the correction control part may control the display to display the reference value when the value output from the gas sensing part is lower than the reference value.

According to another embodiment of the present disclosure, the correction control part may control the display to display the value output from the gas sensing part when the value output from the gas sensing part is higher than the reference value.

According to another embodiment of the present disclosure, the correction control part may control the display so as to provide information corresponding to a step corresponding to the value output from the gas sensing part through the display.

According to another embodiment of the present disclosure, the display may provide additional information corresponding to the displayed value or reference value.

According to another embodiment of the present disclosure, the output value may be a voltage value.

According to another embodiment of the present disclosure, the additional information may be image information.

According to another embodiment of the present disclosure, a speaker providing sound information corresponding to the displayed value or the reference value may be further included.

Advantageous Effects

According to an embodiment of the present disclosure, the output value of the gas sensor which is sensitive to the external environment such as temperature and humidity may be corrected so that the user may more accurately determine whether the gas is detected or not and not be mistaken.

Also according to the embodiment of the present disclosure, the user may more easily recognize the quality of air or the degree of gas contamination.

DESCRIPTION OF DRAWINGS

Embodiments will be described in detail with reference to the following drawings in which like reference numerals refer to like elements, and wherein.

MODES OF THE INVENTION

Figure 1:
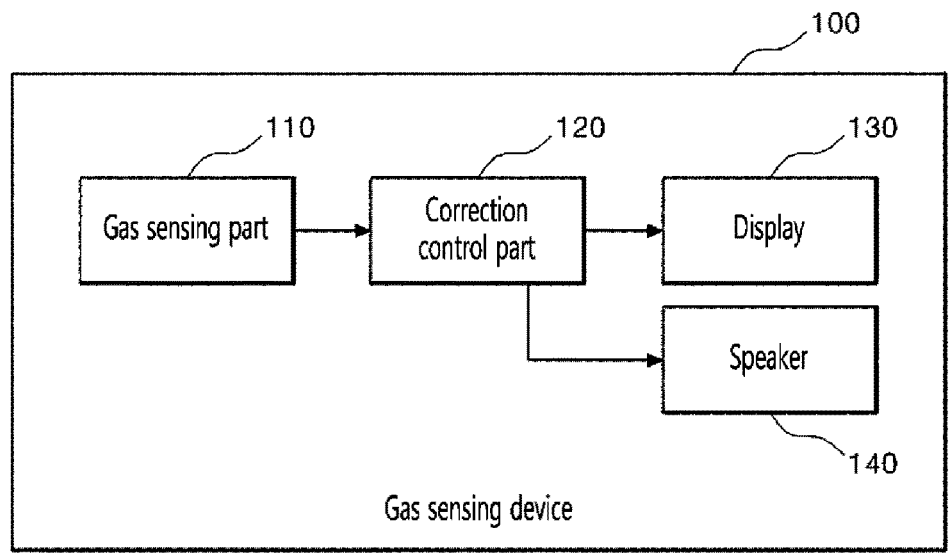
FIG. 1 is a configuration diagram of a gas sensing device according to one embodiment of the present disclosure.

Hereinafter, exemplary embodiments of the present disclosure will be described with reference to the accompanying drawings. Regarding the reference numerals assigned to the elements in the drawings, it should be noted that the same elements may be designated by the same reference numerals, wherever possible, even though they are shown in different drawings. If it is considered that the specific description of the related and noticed functions or structures may obscure the gist of the present invention, the specific description will be omitted. In addition, a thickness of a line, a size of a component and the like, which are shown in the drawings, will be somewhat exaggerated to help clearness of a description and understanding thereof.

Also, in the description of embodiments, terms such as first, second, A, B, (a), (b) or the like may be used herein when describing components of the present disclosure. Each of these terminologies is not used to define an essence, order or sequence of a corresponding component but used merely to distinguish the corresponding component from other component(s). It should be noted that if it is described in the specification that one component is "connected," "coupled" or "joined" to another component, the former may be directly "connected," "coupled" or "joined" to the latter or "connected," "coupled" or "joined" to the latter via another component.

Figure 2:
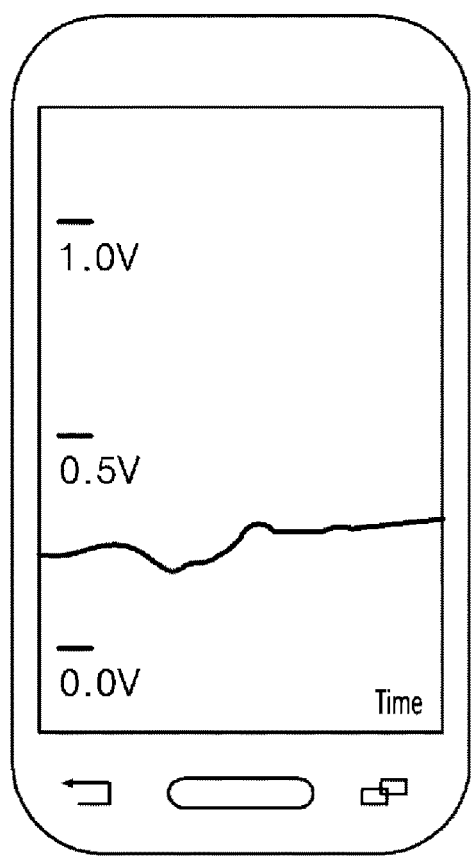
FIGS. 2 to 3 are views illustrating a method of displaying a voltage value of the gas sensing device according to one embodiment of the present disclosure.
Figure 3:
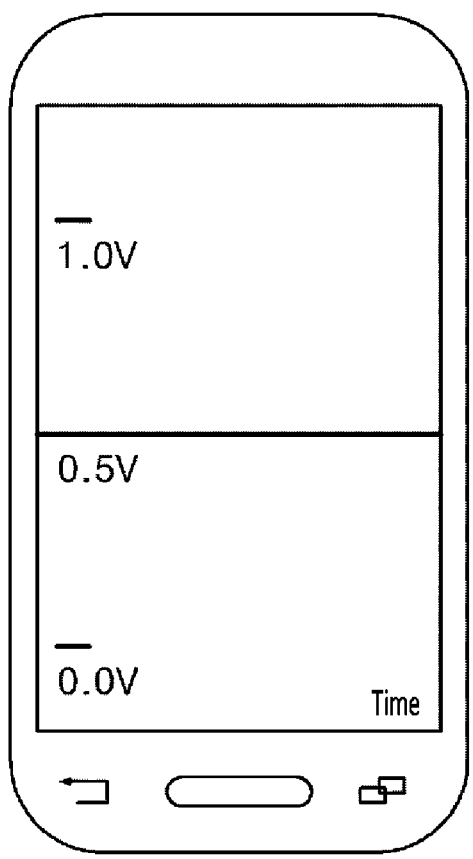

FIG. 1 is a configuration diagram of a gas sensing device according to one embodiment of the present disclosure, and FIGS. 2 to 3 are views illustrating a method of displaying a voltage value of the gas sensing device according to one embodiment of the present disclosure.

With reference to FIGS. 1 to 3, a configuration of a gas sensing device 100 and method of displaying a voltage value according to one embodiment of the present disclosure will be described.

As shown in FIG. the gas sensing device 100 according to one embodiment of the present disclosure includes a gas sensing part 110 and a correction control part 120, and it may be configured with further including a display 130.

The gas sensing part 110 detects gas and outputs a result of sensing the gas.

At this time, the output value may be a voltage value, to this end, the gas sensing part 110 according to one embodiment of the present disclosure includes a resistance and it may be configured to output a voltage through the resistance.

The correction control part 120 changes the value output from the gas sensing part 110 to a reference value.

More specifically, when the value output from the gas sensing part 110 is lower than the reference value, the correction control part 120 may change the output value to the reference value.

That is, the correction control part 120 may constantly correct the value output from the gas sensing part 110 to the reference value.

The display 130 displays gas sensing information.

At this time, the correction control part 120 may control the display 130 to provide information corresponding to a step corresponding to the value output from the gas sensing part 110 through the display 130, and when the value output from the gas sensing part 110 is lower than the reference value, it controls to display the reference value through the display 130.

That is, when the voltage of the gas sensing part 110 is output, the gas sensing part 110 may respond sensitively to minute environmental changes such as temperature or humidity, and an error may occur in the output value. Therefore, when the value output from the gas sensing part 110 is lower than the reference value, the correction control part 120 according to one embodiment of the present disclosure corrects the value output from the gas sensing part 110 and corrects to the same value as the reference value so as to be displayed through the display 130.

For example, in the case in which the value output by the gas sensing part 110 is 0.3 V in a normal gas-free environment, an error of a voltage value of −0.1 V to +0.1 V may occur depending on the influence of temperature or humidity. Therefore, a user may misunderstand that the generated error of −0.1 V to +0.1 V is caused by the detection of gas.

Therefore, according to one embodiment of the present disclosure, as shown in FIG. 2, in the case in which the voltage output from the gas sensing part 110 is 0.3 V, which is lower than the reference value of 0.5 V, as shown in the FIG. 3, the correction control part 120 displays the voltage output from the gas sensing part 110 fixed at 0.5 V through the display 130, and in the case in which the voltage output from the gas sensing part 110 is higher than 0.5 V, the correction control part 120 displays the voltage output from the gas sensing part 110 through the display 130 as it is.

Accordingly, when the reference value of 0.5 V is displayed through the display 130, the user may determine that gas is not detected, and in the case of a voltage equal to or higher than the reference value of 0.5 V (e.g. 0.6 V), since the voltage exceeding the reference value is displayed as it is, the user may correctly determine whether the gas is detected.

TABLE 1

| Range | Display output value | Status information |
|---|---|---|
| Less than 0.5 V | 0.5 V | Good |
| 0.5 V to 1.0 V | Output corresponding voltage value | Normal |
| 1.0 V or more | Output corresponding voltage value | Bad |

Table 1 summarizes that the display method of the display 130 according to the range of the voltage value output from the gas sensing part 110 according to one embodiment of the present disclosure.

As shown in Table 1, in the case in which the voltage value output from the gas sensing part 110 is less than 0.5 V, the display 130 may display 0.5 V and display 'Good' as status information.

Also in the case in which the voltage output from the gas sensing part 110 is 0.5 V to 1.0 V, the display 130 displays the corresponding voltage output from the gas sensing part 110 as it is, and it may display 'Normal" as status information, and in the case in which the voltage value output from the gas sensing part 110 exceeds 1.0 V, the display 130 displays the corresponding voltage output from the gas sensing part 110 as it is, and it may display 'Bad' as status information.

In addition, the gas sensing device 100 according to one embodiment of the present disclosure may further include a speaker 140, and sound information corresponding to the voltage value output from the gas sensing part 110 may be provided through the speaker 140 so that the user may more easily recognize a quality of air or a degree of gas contamination.

Figure 4:
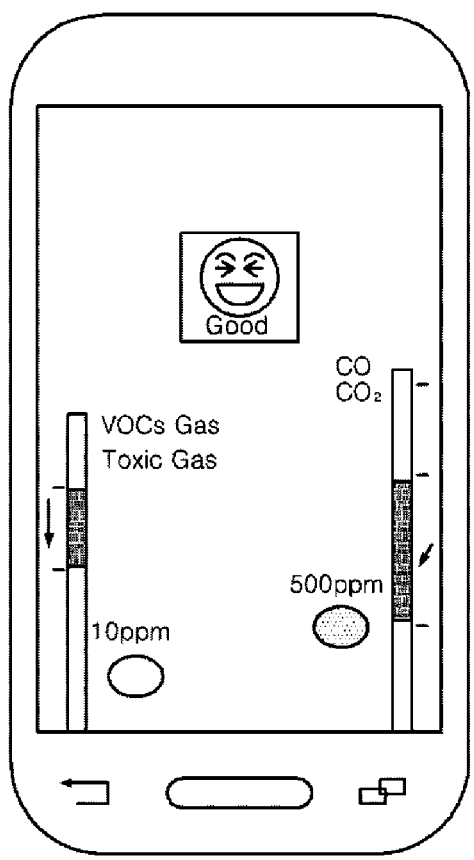
FIGS. 4 to 5 are views for describing an information providing method of the gas sensing device according to one embodiment of the present disclosure.
Figure 5:
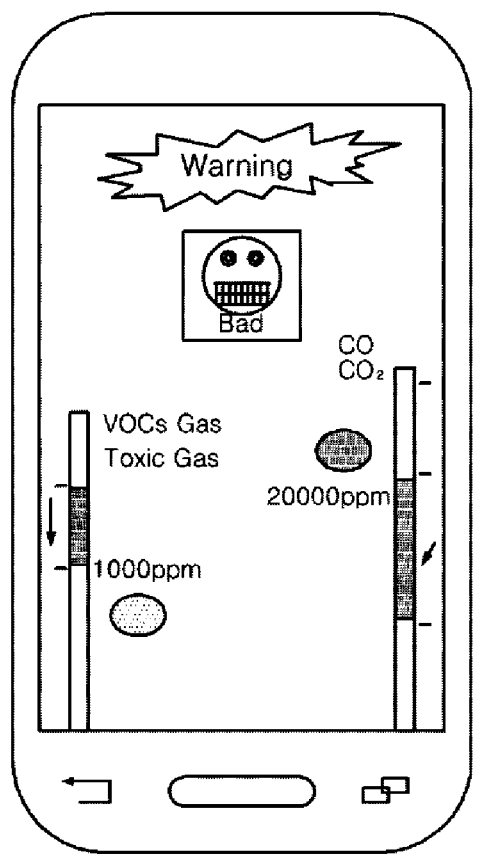

FIGS. 4 to 5 are views for describing an information providing method of the gas sensing device according to one embodiment of the present disclosure.

As shown in FIGS. 4 to 5, the gas sensing device 100 according to one embodiment of the present disclosure may be configured such that the display 130 may provide additional information corresponding to a corresponding voltage output from the gas sensing part 110.

That is, in the case in which the gas sensing device 100 according to one embodiment of the present disclosure detects gas, the type and concentration of the detected gas may be displayed.

Also, the gas sensing device 100 displays in image so as to more easily recognize information corresponding to the type and concentration of the detected gas, and it may provide sound information corresponding to the type and concentration of the detected gas through the speaker 140.

Meanwhile, the gas sensing device 100 according to one embodiment of the present disclosure may be configured as a portable terminal.

Figure 6:
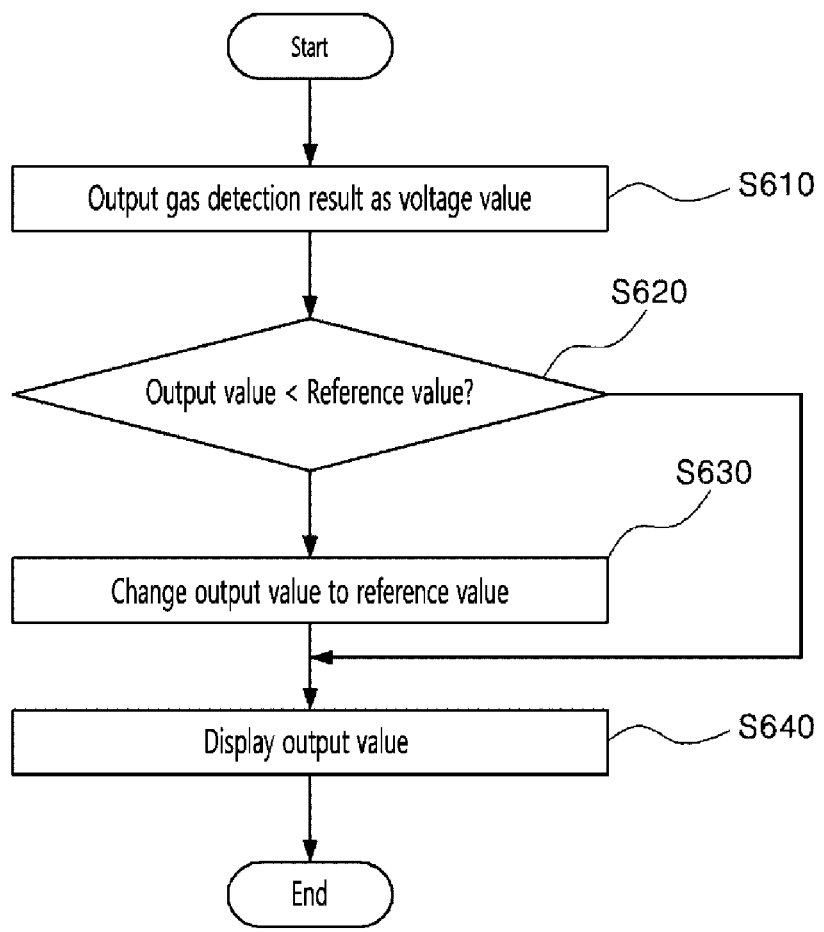
FIG. 6 is a flowchart for describing an operation method of the gas sensing device according to one embodiment of the present disclosure.

FIG. 6 is a flowchart for describing an operation method of the gas sensing device according to one embodiment of the present disclosure.

With reference to FIG. 6, an operation method of the gas sensing device 100 according to one embodiment of the present disclosure will be described.

First, when the gas sensing part 110 detects gas, it outputs a result of detecting the gas (S610).

To this end, the gas sensing part 110 according to one embodiment of the present disclosure includes resistance and it may be configured to output the detected result as a voltage value through the resistance.

Thereafter, the correction control part 120 determines whether the value output from the gas sensing part 110 is lower than a reference value or not (S620).

As a result of the determination, when a value output from the gas sensing part 110 is lower than a reference value, the correction control part 120 changes and corrects the value to be the reference value (S630).

That is, when the voltage of the gas sensing part 110 is outputted, an error may occur in the output voltage since the gas sensing part 110 sensitively responses to a minute environmental change such as temperature or humidity. Therefore, according to one embodiment of the present disclosure, a voltage value output from the gas sensing part 110 is lower than a reference value, the correction control part 120 corrects the voltage value output from the gas sensing part 110 to the same value as the reference value.

Thereafter, the correction control part 120 controls so as to display the corrected output value through the display 130 as described above (S640).

Meanwhile, as the result of determination, when the value output from the gas sensing part 110 is higher than the reference value, the correction control part 120 may control so as to display the value output from the gas sensing part 110 through the display 130.

In addition, the gas sensing device 100 according to one embodiment of the present disclosure may provide additional information corresponding to a corresponding voltage output from the gas sensing part 110, and more specifically, when gas is detected, the type and concentration of the detected gas may be displayed.

In addition, the gas sensing device 100 displays in image so as to more easily recognize the information corresponding to the type and concentration of the detected gas, and it may provide sound information corresponding to the type and concentration of the detected gas through the speaker 140.

Therefore, according to the embodiment of the present disclosure, by correcting the output value of a gas sensor which is sensitive to the external environment such as temperature and humidity, the user may more accurately determine whether the gas is detected or not and not be mistaken.

Also, according to the embodiment of the present disclosure, the user may more easily recognize the quality of air or the degree of gas contamination.

In the foregoing detailed description of the present disclosure, specific examples have been described. However, various modifications are possible within the scope of the present disclosure. The technical spirit of the present disclosure should not be limited to the described embodiment of the present disclosure, but should be determined by not only the scope of the appended claims but also the equivalents to the claims.

EXPLANATION OF SYMBOLS

100: Gas sensing device
110: Gas sensing part
120: Correction control part
130: Display
140: Speaker

The invention claimed is:

1. A gas sensing device comprising:
    a gas sensing part configured to sense for gas and output an output voltage based on the sensed gas; and
    a control part that receives the output voltage from the gas sensing part and configured to output a result value based on the output voltage,
    wherein the control part compares the output voltage to a reference voltage, and
    when the control part determines that the output voltage from the gas sensing part is less than the reference voltage, the control part changes a display of the result value by providing the reference voltage as the result value, and
    when the control part determines that the output voltage from the gas sensing part is greater than or equal to the reference voltage, the control part controls the display to output the output voltage received from the gas sensing part as the result value.

2. The gas sensing device according to claim 1, wherein when the control part determines that the output voltage from the gas sensing part is less than the reference voltage, the control part constantly changes the display by constantly changing the result value from the output voltage to the reference voltage.

3. The gas sensing device according to claim 1, further comprising a display for displaying gas detection information,
    wherein when the control part determines that the output voltage from the gas sensing part is less than the reference voltage, the control part controls the display to display the result value based on the reference voltage.

4. The gas sensing device according to claim 3, wherein when the control part determines that the output voltage from the gas sensing part is greater than or equal to the reference voltage, the control part controls the display to display the result value based on the output voltage from the gas sensing part.

5. The gas sensing device according to claim 3, wherein the display provides additional information corresponding to the displayed result value.

6. The gas sensing device according to claim 5, wherein the additional information is image information.

7. The gas sensing device according to claim 6, wherein when the result value is the reference voltage, the additional information indicates that gas is not present, when the result value is between the reference voltage and a first prescribed voltage, the additional information indicates that gas is present within an acceptable level, and when the result value is greater than the first prescribed voltage, the additional information indicates a warning for presence of gas.

8. The gas sensing device according to claim 7, wherein the first prescribed voltage is 1.0 V.

9. The gas sensing device according to claim 5, further comprising a speaker for providing sound information corresponding to the displayed result value.

10. The gas sensing device according to claim 1, wherein the reference voltage corresponds to an output voltage level of the gas sensing part associated with a state in which gas is not detected.

11. The gas sensing device according to claim 1, wherein the gas sensing part is affected by humidity and temperature such that the output voltage has a prescribed error value.

12. The gas sensing device according to claim 11, wherein the reference voltage is greater than the prescribed error value.

13. The gas sensing device according to claim 12, wherein the prescribed error value is −0.1 V to +0.1 V and the reference voltage is 0.5 V.

14. A gas sensing device comprising:

a gas sensing part configured to sense for presence of gas and output an output voltage based on sensed concentration of gas;

a control part that receives the output voltage from the gas sensing part and configured to output a result value based on the output voltage; and a display configured to display gas detection information including the result value, wherein the control part compares the output voltage to a reference voltage, and when the control part determines that the output voltage from the gas sensing part is less than the reference voltage, the control part changes the display of the result value by displaying the reference voltage as the result value, and when the control part determines that the output voltage from the gas sensing part is greater than or equal to the reference voltage, the control part controls the display to display the output voltage received from the gas sensing part as the result value, wherein the gas sensing part is affected by humidity and temperature such that the output voltage has a prescribed error value, and wherein the reference voltage is greater than the prescribed error value.

* * * * *